US00PP37684P2

(12) United States Plant Patent
Klemm et al.

(10) Patent No.: US PP37,684 P2
(45) Date of Patent: Sep. 8, 2026

(54) ***DIANTHUS* PLANT NAMED 'KLEDG20460'**

(50) Latin Name: ***Dianthus* sp.**
Varietal Denomination: KLEDG20460

(71) Applicant: KLEMM + SOHN GMBH & CO. KG, Stuttgart (DE)

(72) Inventors: Nils Klemm, Stuttgart (DE); Lena Thiede, Riederich (DE)

(73) Assignee: KLEMM + SOHN GMBH & CO. KG, Stuttgart (DE)

( * ) Notice: Subject to any disclaimer, the term of this patent is extended or adjusted under 35 U.S.C. 154(b) by 0 days.

(21) Appl. No.: 19/346,915

(22) Filed: Oct. 1, 2025

(51) Int. Cl.
*A01H 5/02* (2018.01)
*A01H 6/30* (2018.01)

(52) U.S. Cl.
USPC ..... Plt./281

(58) Field of Classification Search
USPC ..... Plt./272, 273, 281
See application file for complete search history.

(56) References Cited

PUBLICATIONS https://www.perennials.com/plants/dianthus-caryophyllus-pink-kisses.html. Retrieved form the Internet on Jan. 29, 2026.*

* cited by examiner

*Primary Examiner* — Susan Mccormick Ewoldt
(74) *Attorney, Agent, or Firm* — Weatherly IP Solutions, LLC; James M. Weatherly

(57) ABSTRACT

A new *Dianthus* plant designated 'KLEDG20460' particularly distinguished by double pink flowers with purple centers and very early flowering; is disclosed.

1 Drawing Sheet

Genus and species: *Dianthus* sp.
Variety denomination: 'KLEDG20460'.

BACKGROUND

The present invention comprises a new and distinct variety of *Dianthus*, botanically known as *Dianthus* sp., and hereinafter referred to by the variety name 'KLEDG20460'. 'KLEDG20460' originated from a whole plant mutation from the *Dianthus* parent 'KLEDG12163' (U.S. Plant Pat. No. 24,707) in June 2018 in The Netherlands.

In September 2018, 'KLEDG20460' was first vegetatively propagated by vegetative stem cuttings in Stuttgart Germany, and subsequently in Latina, Italy. 'KLEDG20460' was found to reproduce true to type in successive generations of asexual propagation in Stuttgart, Germany and Latina, Italy via vegetative stem cuttings.

SUMMARY

The following are the most outstanding and distinguishing characteristics of 'KLEDG20460' when grown under normal horticultural practices in Stuttgart, Germany.

1. Double, pink flowers with purple centers; and
2. Very early flowering.

DESCRIPTION OF THE PHOTOGRAPH

This new *Dianthus* plant is illustrated by the accompanying photograph which shows an overall view a whole plant of 'KLEDG20460' showing foliage, buds, and flowers.

The photo is of a 30-week-old plant taken in May 2019 in a greenhouse in Stuttgart, Germany. The colors shown are as true as can be reasonably obtained by conventional photographic procedures.

DESCRIPTION OF 'KLEDG20460'

The following detailed descriptions set forth the distinctive characteristics of 'KLEDG20460'. The data which define these characteristics were collected from asexual reproductions carried out in Stuttgart, Germany. Data was collected in May 2019 on 7-month old plants grown in a plastic greenhouse. Color references are to The R.H.S. Colour Chart of The Royal Horticultural Society of London (R.H.S.), 5$^{th}$ edition (2007).

Classification:
- *Family.*—Caryophyllaceae.
- *Botanical.*—*Dianthus* sp.
- *Common.*—Pot carnation.
- *Designation.*—'KLEDG20460'.

Parentage: Mutation of the proprietary *Dianthus* 'KLEDG12163' (U.S. Plant Pat. No. 24,707).

Plant:
- *Propagation type.*—Vegetative cuttings via stem, terminal cuttings.
- *Time to produce a rooted young plant.*—10 to 14 days.
- *Root description.*—Fine roots, young roots are RHS 161D, mature roots are RHS 199C.
- *Rooting habit shape.*—Deep rooting.
- *Plant form.*—Upright.
- *Plant height.*—15 cm to 17 cm.
- *Plant diameter or spread.*—22 cm to 25 cm.

Lateral branches:
- *Length.*—7 cm to 10 cm.
- *Diameter.*—4 cm to 7 cm.
- *Internode length.*—2 cm to 3 cm.
- *Number of internodes per branch/stem.*—3 to 5.
- *Node length.*—0.2 cm to 0.4 cm.
- *Node diameter.*—0.2 cm to 0.4 cm.

*Texture.*—Smooth.
*Color.*—RHS 146B.
*Branch/stem appearance in cross-section.*—Solid.

Foliage:
*Arrangement.*—Opposite.
*Length.*—4 cm to 5 cm.
*Width.*—0.3 cm to 0.5 cm.
*Shape.*—Lanceolate.
*Apex.*—Acute.
*Base.*—Obtuse.
*Margin.*—Entire.
*Texture* (*both upper and lower surfaces*).—Smooth.
*Leaf color.*—Upper surface: RHS 138A for immature leaves and RHS 137A for mature leaves Lower surface: RHS 138A for immature leaves and RHS 137A for mature leaves
*Venation pattern.*—Absent.

Flowers:
*Flower type and habit.*—Semi-double, small sprays, round.
*Fragrance.*—Present.
*Natural flowering season.*—Spring to autumn.
*Position of flowers relative to the foliage.*—Moderately above.
*Number of flowers per spray.*—3 to 5.
*Flower longevity on the plant.*—14 to 18 days.

Buds:
*Length.*—0.5 cm to 1.5 cm.
*Diameter.*—0.3 cm to 0.4 cm.
*Shape.*—Elliptic.
*Color.*—RHS 138A.
*Extrusion of the styles at the bud stage.*—Absent.

Corolla:
*Quantity of petals and arrangement.*—7 to 13 and arranged in several whorls.
*Corolla height.*—0.8 cm to 1.5 cm.
*Petal length.*—1.8 cm to 2.5 cm.
*Petal width.*—1.0 cm to 1.5 cm.
*Petal shape.*—Spoon-shaped.
*Petal apex.*—Obtuse.
*Petal base.*—Acute.
*Petal margin.*—Serrated.
*Depth of petal margin.*—Shallow.
*Petal texture* (*both upper and lower surfaces*).—Smooth.
*Petal color* (*both immature and mature*).—Upper surface: Immature petals: RHS 72C and RHS 79B Mature petals: RHS 75A and RHS 79C Lower surface: RHS 75D
*Calyx.*—Quantity of sepals and arrangement: Composed of 5 sepals Shape: Campanulate Calyx height: 0.8 cm to 1.5 cm Calyx diameter (at the apex): 0.4 cm to 0.6 cm
*Sepal texture* (*both upper and lower surfaces*).—Smooth.
*Sepal color.*—Upper surface: RHS 137A Lower surface: RHS 137D Peduncles:
*Length.*—5 cm to 8 cm.
*Diameter.*—0.2 cm.
*Strength.*—Moderate.
*Texture.*—Smooth.
*Color.*—RHS 146B.

Reproductive organs:
*Stamens.*—Quantity per flower: Moderate Filament length: 0.5 cm to 0.8 cm Filament color: RHS 157B Anther length: 0.1 cm Anther diameter: 0.05 cm Anther color: RHS 155B Pollen amount: Absent
*Pistils.*—Not observed.

Fruit and seed set: Not observed.

Disease and pest/insect resistance: No disease and pest/insect resistance observed.

COMPARISON OF 'KLEDG20460' WITH PARENTAL LINE AND KNOWN VARIETY

'KLEDG20460' is distinguished from the mutation parent as described in Table 1.

TABLE 1

Comparison with Parental Line

| Characteristic | 'KLEDG20460' | Mutation Parent 'KLEDG12163' |
|---|---|---|
| Main flower color | RHS 81C | RHS 75B |
| Secondary flower color | RHS 79B | RHS 71A |
| Flower color pattern | Bi-color | Bi-color |
| Flower diameter | Larger flower diameter than 'KLEDG12163' | Smaller flower diameter than 'KLEDG20460' |

'KLEDG20460' can be compared to the commercial Dianthus variety 'KLEDG18305' (U.S. Plant Pat. No. 31,019). Differences between the varieties are described in Table 2.

TABLE 2

Comparison with Similar Variety

| Characteristic | 'KLEDG20460' | 'KLEDG18305' |
|---|---|---|
| Flower type | Double | Single |
| Flower color | Pink with purple center | Pink with purple ring |
| Flowering time | Very early | Early-medium |

We claim:

1. A new and distinct cultivar of Dianthus plant designated 'KLEDG20460' as illustrated and described herein.

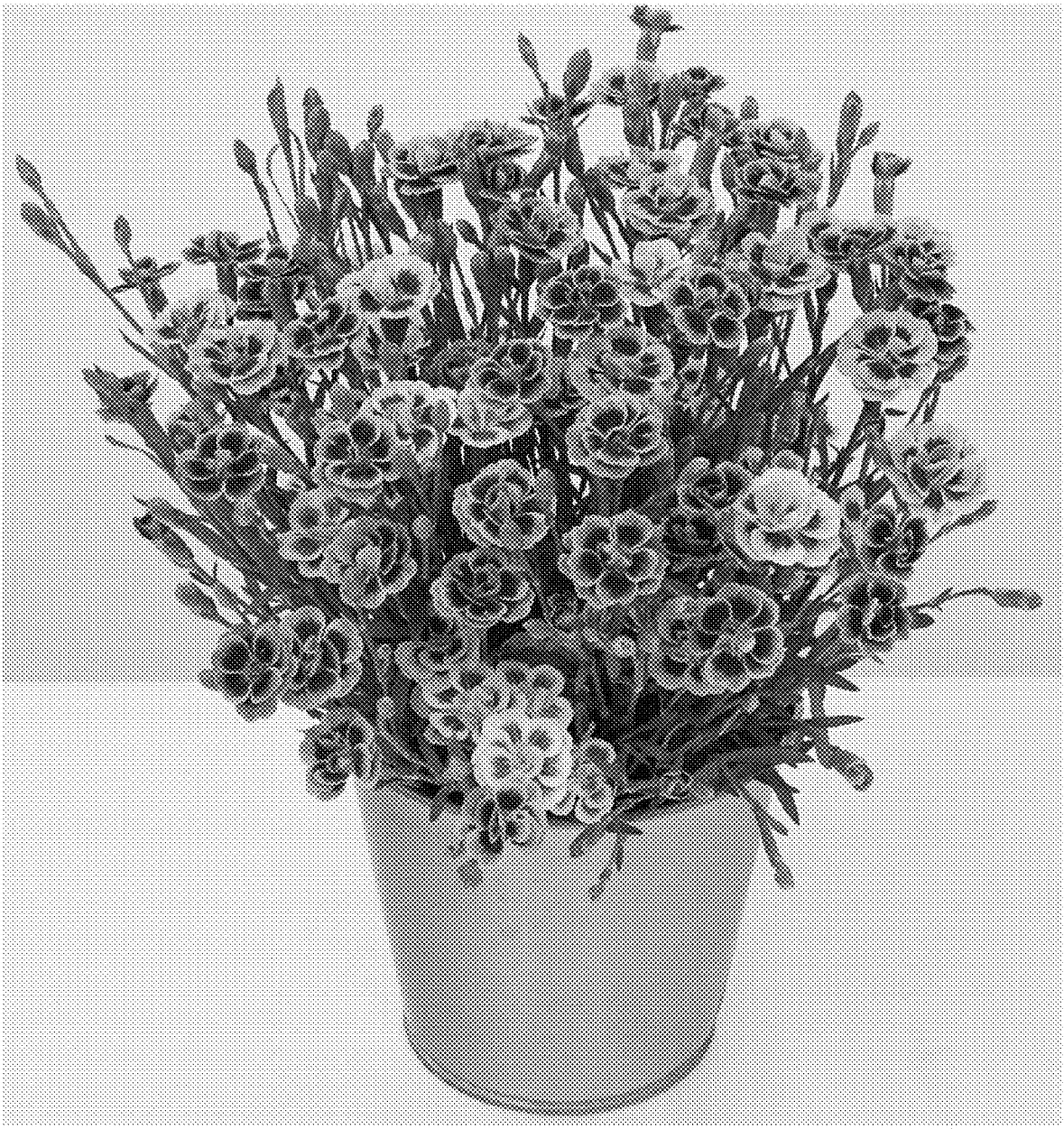

* * * * *